(12) United States Patent
Sim et al.

(10) Patent No.: US 8,473,085 B2
(45) Date of Patent: Jun. 25, 2013

(54) MUTEX-MEDIATED CONTROL OF SPATIAL ACCESS BY APPLIANCES MOVEABLE OVER A COMMON PHYSICAL SPACE

(75) Inventors: James Sim, Evergreen Park, IL (US); Todd Stephan, Aurora, IL (US); Bruce Tyley, La Grange, IL (US)

(73) Assignee: PerkinElmer LAS, Inc., Waltham, MA (US)

( * ) Notice: Subject to any disclaimer, the term of this patent is extended or adjusted under 35 U.S.C. 154(b) by 1423 days.

(21) Appl. No.: 12/112,466

(22) Filed: Apr. 30, 2008

(65) Prior Publication Data

US 2009/0276071 A1 Nov. 5, 2009

(51) Int. Cl.
*G06F 19/00* (2011.01)
*G05B 19/418* (2006.01)

(52) U.S. Cl.
USPC ............................................. 700/99; 700/248

(58) Field of Classification Search
USPC ............... 700/99, 248; 901/8, 49; 324/76.52, 324/76.77; 327/10, 12, 2, 3, 40, 5, 7, 8; 710/200; 718/100, 102, 103, 104, 106, 107, 718/108; 331/16, 1 A, 25
See application file for complete search history.

(56) References Cited

U.S. PATENT DOCUMENTS

| | | | | |
|---|---|---|---|---|
| 5,443,791 A * | 8/1995 | Cathcart et al. | ................... | 422/65 |
| 6,132,582 A * | 10/2000 | King et al. | ..................... | 204/604 |
| 6,326,147 B1 * | 12/2001 | Oldham et al. | .............. | 435/6.12 |
| 6,721,615 B2 * | 4/2004 | Fava et al. | ........................ | 700/99 |
| 7,114,157 B2 * | 9/2006 | Chaffee et al. | ................. | 718/104 |
| 2002/0059558 A1 * | 5/2002 | Hines | ............................ | 717/103 |

* cited by examiner

*Primary Examiner* — Ian Jen
(74) *Attorney, Agent, or Firm* — Cesari and McKenna, LLP (57) ABSTRACT

A configurable mutual exclusion function oversees movement of appliances mobile over a common physical space in an automated laboratory workstation. A configurable mutex is allotted for each moveable appliance and is configurable to protect a task site when obtained for the respective appliance.

20 Claims, 6 Drawing Sheets

MUTEX-MEDIATED CONTROL OF SPATIAL ACCESS BY APPLIANCES MOVEABLE OVER A COMMON PHYSICAL SPACE

BACKGROUND OF THE INVENTION

1. Field of the Invention

The invention pertains to robotic devices. In particular, this invention provides method and apparatus for managing multiple moveable robotic devices sharing a physical space.

2. Background Information

Automated laboratory workstations, such as are used for biochemical assays, generally have several tools that need access in turn to the same physical location. A computer system controls the tools to perform one or more procedures chosen by a user. A single procedure commonly entails component tasks to be completed by more than one of the tools, at various locations around the workstation platform. Scheduling software organizes the component tasks of all the chosen procedures into an agenda.

When the computer system executes the agenda so that tool movements are performed serially in a predetermined coordinated sequence, avoiding collisions between tools is relatively straightforward, since the tools do not act concurrently. However, requiring all but one tool to be idle at any given time—even if the other tools need to perform tasks in non-overlapping sections of the workspace—slows the completion of procedures.

An alternative approach would involve generating, from the agenda, a dedicated routine for each of the tools and allowing the tools to carry out their routines concurrently, so that distinct tasks could be performed simultaneously. However, such parallel execution introduces the possibility of collision between tools as two or more tools independently attempt to occupy the same physical location in the platform simultaneously. Collision prevention in this case would require complex scheduling algorithms that essentially choreograph the entire procedure.

SUMMARY OF THE INVENTION

A system for controlling moveable robotic devices uses a configurable mutual exclusion ("mutex") control processor, or function, to manage access by moveable devices to physical space. In particular, the mutex control function manages access to a protected physical space by tools or other moveable devices based on the possession and coverage of configurable mutexes.

In a computer-implemented system for managing multiple appliances moveable over a common physical space, the invention can be used to prohibit one appliance from attempting to occupy a position already occupied by, or about to be occupied by, another appliance. The one-at-a-time access to automated workstation workspace dynamically enforced by the mutex protection obviates collisions between appliances performing independent operations, without necessitating complex scheduling algorithms.

In an automated laboratory workstation, the capacity to obtain the mutexes, and to configure them to protect a portion of the common space, resides in the workstation computer system, independent of any scheduling function. The dynamic management of workspace access by the mutex control function frees the scheduling function from having to make any advance provision for preventing collisions between appliances. Because of the independence of the mutex-control function from the scheduling formula, the routines instructing different appliance controllers need not even be implemented by copies of the same interpreter application. The ability of the mutex-control feature to oversee collision avoidance without coordination by the scheduling function or interpreter applications increases the efficiency and flexibility of the automated workstation.

BRIEF DESCRIPTION OF THE DRAWINGS

The invention description below refers to the accompanying drawings, of which.

Features in the drawings are not, in general, drawn to scale.

DETAILED DESCRIPTION OF AN ILLUSTRATIVE EMBODIMENT

Figure 1:
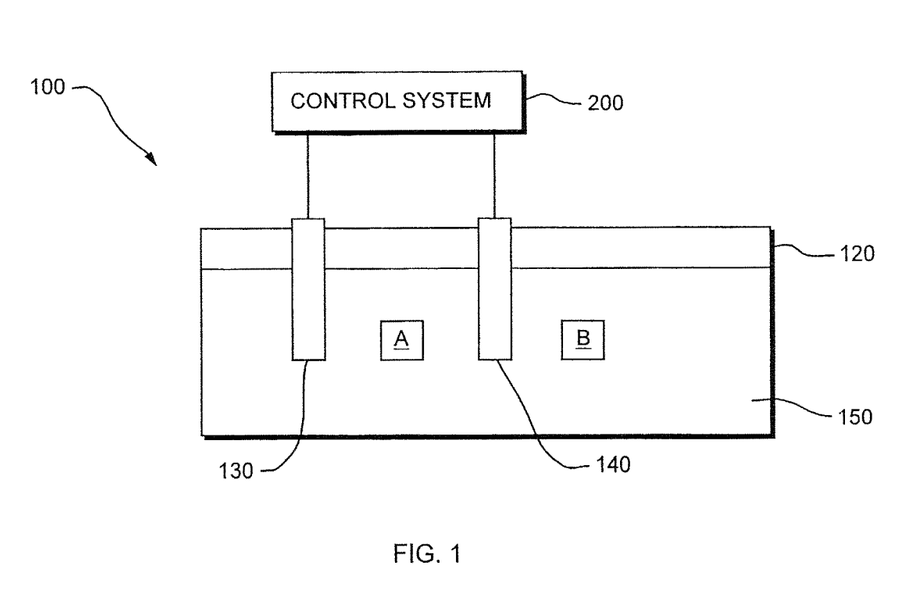
FIG. 1 is an overhead schematic view of a biochemistry laboratory automated workstation compatible with the invention.

With reference to FIG. 1, an exemplary automated laboratory workstation 100 has a track 120 along which two appliances are mobile: a robotic pipetting arm 130 and a robotic gripper arm 140. The robotic pipetting arm 130 operates a pipetting tool which dispenses and aspirates liquid and may be supported by ancillary tools, for example, a pump and a reagent reservoir, which are not shown. The robotic gripper arm 140 includes a gripping tool and transports labware around the workstation or to a peripheral device such as a reader, a washer, or a temperature control unit. The appliances extend and carry out operations over the workspace 150. In the example, the appliances operate to carry out various tasks associated with biochemical assays as directed by the control system 200.

Figure 2:
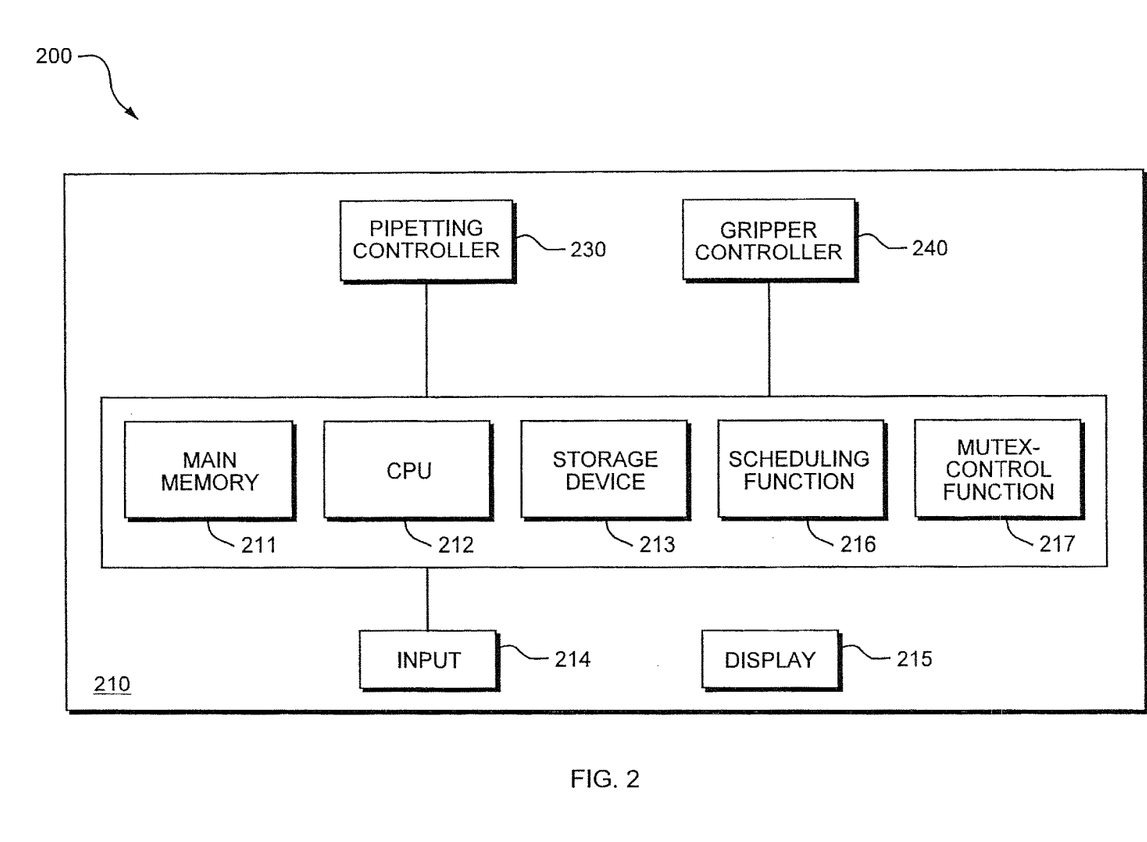
FIG. 2 is a block-diagram view of a representative hardware system compatible with the invention.

With reference to FIG. 2, the control system 200 comprises a computer system 210 operatively connected to a pipetting controller 230 and a gripper controller 240, which communicate with the robotic pipetting arm 130 and the robotic gripper arm 140, respectively, via external controllers for the appliances.

The computer system 210 is programmable and includes a main memory 211, a central processing unit 212, and a storage device 213, operatively coupled to an input device 214 and a display 215. A graphical user interface, software programs, and procedure parameters may be stored in the main memory 211.

The computer system 210 also comprises a scheduling processor, or function, 216 which is adapted to create an agenda from parameters defining one or more procedures chosen by a user or stored in memory. A procedure generally entails component tasks to be completed by both the gripper and the pipetting tools. The agenda accounts for procedure-essential timing requirements such as residence time at a site for a single appliance or ordering constraints governing joint endeavors between appliances such as, for example, access to respective specimens. The agenda does not regard whether or not multiple appliances are called on to occupy the same space simultaneously.

Based on the agenda, the scheduling function also produces, for each of the needed appliances, a task list, or routine. Each task in a routine includes an operation and a site at which the operation is to be accomplished. The pipetting routine is interpreted by the pipetting controller 230, which operates the pipetting robotic arm 130 to accomplish the tasks associated with the agenda. The gripper routine is similarly interpreted by the gripper controller 240, which operates the robotic gripper arm 140.

The computer system 210 further comprises a mutex-control system, or function, 217, which is adapted to allot a pipetting mutex for the pipetting controller 230 and a gripper mutex for the gripper controller 240. Each appliance-specific mutex, which is configurable to protect a region of space, or target zone, is obtainable for the appliance if no other appliance holds a mutex protecting any portion of that region of space. The mutex control function configures the mutexes as needed by the controllers 230 and 240, to protect target zones to be accessed by the pipetting arm 130 and the gripper arm 140, respectively. By obtaining and releasing mutexes protecting the target zones, the mutex-control function 217 prevents collisions between the pipetting arm 130 and the gripper arm 140 while allowing them to work simultaneously and independently when they do not require access to the same portion of the workspace 150.

FIGS. 3A-3H depict the locations along the axis 305 of the pipetting arm 130 and the gripper arm 140 over the course of a user-specified procedure. The horizontal axis 305 is labeled with numerals indicating arbitrary units of distance along the track 120 of the workstation 100. Respective requested target zones and mutexes held for the pipetting arm 130 and the gripper arm 140 are indicated above the space representing the appliance locations. The procedure entails the following tasks: the gripper arm 140 operates at position 8 to perform a task over region B of FIG. 1 and next operates at position 4 to perform a task over region A of FIG. 1; and the pipetting arm 130 operates at position 4 to perform a task over region A of FIG. 1. The scheduling function 216 generates routines for each of the controllers 230 and 240.

Figure 3A:
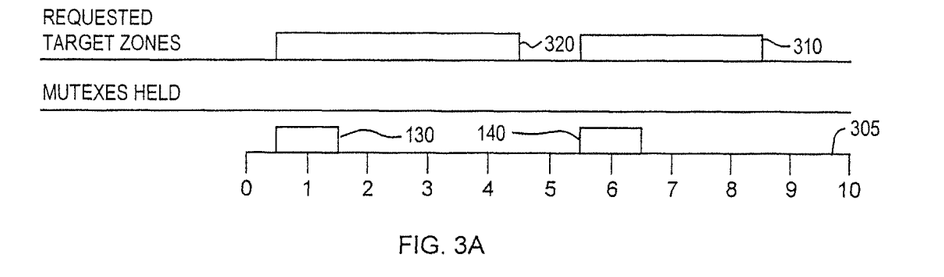
FIGS. 3A-3H illustrate a procedure scenario for the automated laboratory workstation of FIG. 1.
Figure 3B:
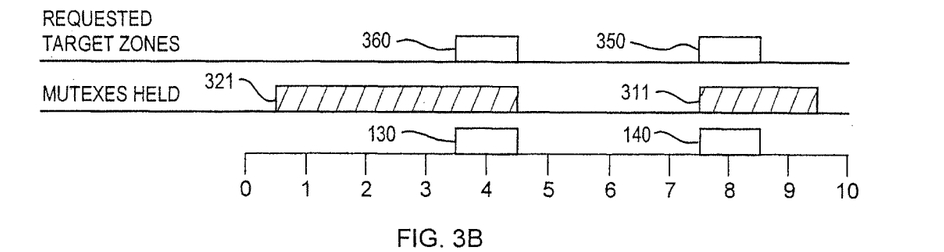

With reference to FIGS. 3A-B, in a starting configuration the pipetting arm 130 is at position 1 and the gripper arm 140 is at position 6. Neither the pipetting arm 130 nor the gripping arm 140 holds any mutex protecting locations along the track 120. Before moving the gripper arm 140 to position 8, the target site for the initial task, the gripper controller 240 confers with the mutex control function 217 in the computer system 210 to determine whether the function 217 can obtain for the controller 240 a gripper mutex protecting the gripper target zone 310, which encompasses at least locations from position 6 to position 8. Since no pipetting mutex is configured, there is no impediment to the mutex control function's configuring and obtaining a gripper mutex protecting target zone 310, and the mutex control function communicates the same to the gripper controller 240. The mutex obtained for the gripper arm 140 is denoted by reference numeral 311. The gripper controller 240 then begins moving the gripper arm 140 to position 8.

The pipetting controller 230 similarly requests a pipetting mutex protecting a pipetting target zone 320, which encompasses at least locations from position 1 to position 4. Because the target zone requested by the pipetting controller 230 does not overlap the gripper target zone protected by mutex 311, the mutex function configures and obtains for the pipetting controller 230 a pipetting mutex 321 for the requested target zone 320. The appliances are then able to work on their tasks concurrently.

FIG. 3B depicts the workstation 100 with the gripper arm 140 at the target gripper site, position 8, and the pipetting arm 130 at the pipetting target site, position 4. Once the gripper arm 140 has completed travel along the pathway to the gripper target site, position 8, the gripper controller 240 notifies the mutex control function 217. This notification serves as a request to the mutex control function 217 to reconfigure the gripper mutex 311 to include a reduced target zone 350, corresponding to the gripper target site. Likewise, the pipetting controller 230 sends a "relocation complete" signal to the mutex control function 217 after it has re-located to the pipetting target site, or position 4, thereby requesting, in effect, a reconfiguration of the pipetting mutex to protect a reduced target zone 360.

Figure 3C:
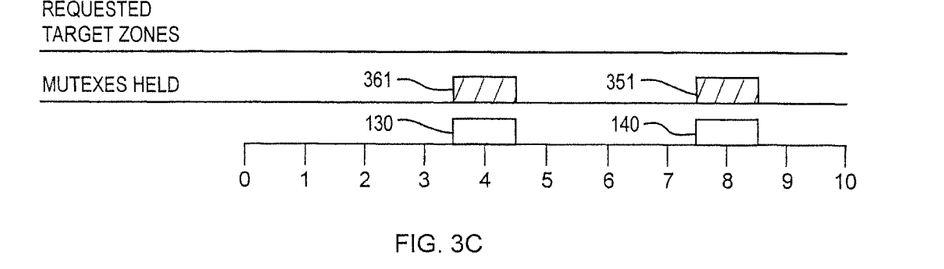

FIG. 3C depicts the gripper arm 140 operating at position 8 and the pipetting arm 130 operating at position 4, and denotes target zones protected by the gripper and pipetting mutexes as shaded areas 351 and 361, respectively. The reconfigured mutex 351 protecting a reduced target zone frees for use by another appliance the pathway including location 6 up to location 8.

Figure 3D:
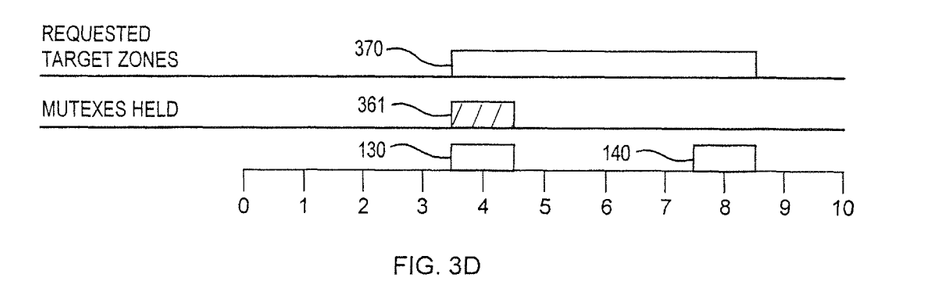

In FIG. 3D, the gripper arm 140 has completed its task at position 8. In response to a "task complete" signal from the gripper arm controller 240, the mutex control function 217 releases the gripper mutex 351 so that the site of the completed task, position 8, is no longer protected. In order to begin the next gripper task on the gripper routine, the gripper controller 240 again confers with the mutex control function 217, to request a gripper mutex to protect a target zone 370 that includes a target site at position 4 and a pathway to relocate to position 4.

The pipetting arm 130 continues operation at position 4, with the pipetting mutex 361 still protecting the pipetting site. Accordingly, the mutex-control function 217 queues the gripper controller's request for a gripper mutex, and thus defers travel by the gripper arm 140 to the gripper target site.

Figure 3E:
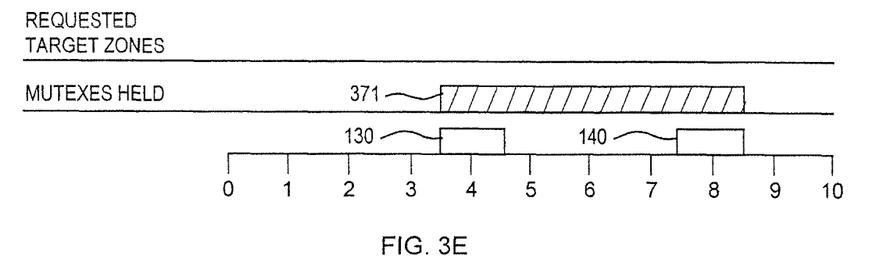

In FIG. 3E, the pipetting arm 130 has completed its task at position 4, and sends a "task complete" signal to the mutex-control function 217 so the pipetting mutex 360 can be released. Upon release of the pipetting mutex 360, the mutex control function 217 processes the queued request for a gripper mutex to protect locations 8 to 4. Since the pipetting arm 130 is residing at position 4, the gripper controller 240 may direct the pipetting controller 230 to move the pipetting arm 130 out of the target zone protected by the gripper mutex 371. The gripper controller may, for example, broadcast a direction to vacate the target zone. Alternatively, the mutex control function 217 may signal the pipetting controller 230 to move the pipetting arm 130 out of the protected target zone.

Figure 3F:
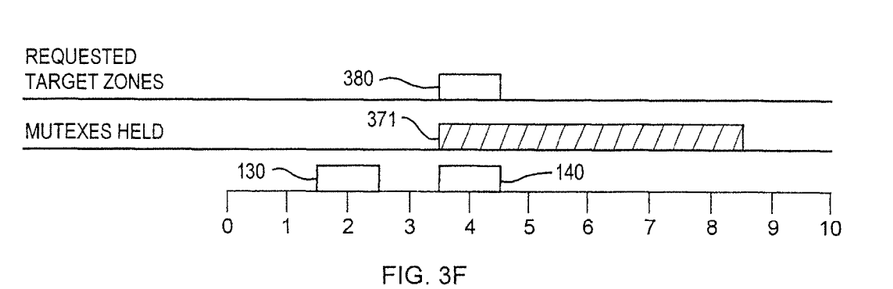

In FIG. 3F, the pipetting arm 130 has vacated the protected target zone, and moved to position 2. The gripper arm 140 has moved to position 4 under the gripper mutex 371. After arrival at the target site 4, the gripper controller 240 notifies the mutex control function 217, in effect requesting reconfiguration of the gripper mutex to protect a reduced target zone 380, corresponding to the task site, namely, position 4.

Figure 3G:
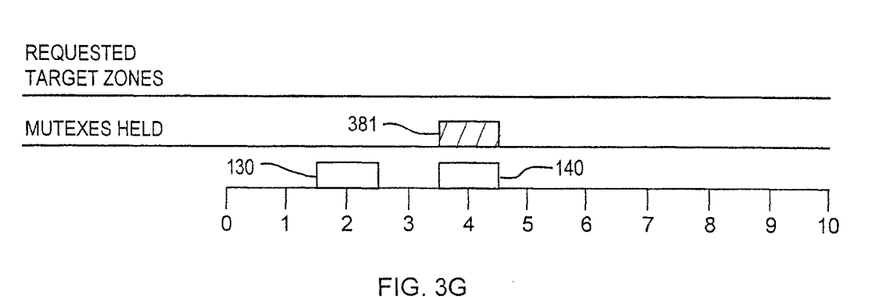

In FIG. 3G, the gripper arm 140 operates at position 4, protected by the reconfigured gripper mutex 381. When the gripper arm 140 completes its task at the site, the gripper controller 240 signals the mutex-control function 217, and the mutex-control function 217 releases the gripper mutex 381.

Figure 3H:
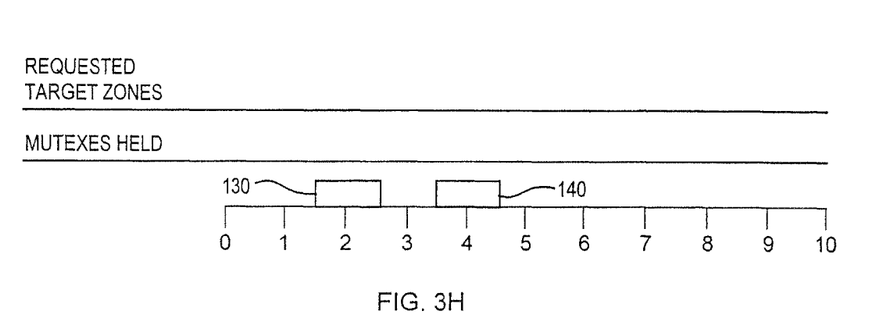

FIG. 3H shows the pipetting arm 130 and gripper arm 140 in their final positions at the end of the procedure. All mutexes have been released.

Figure 4:
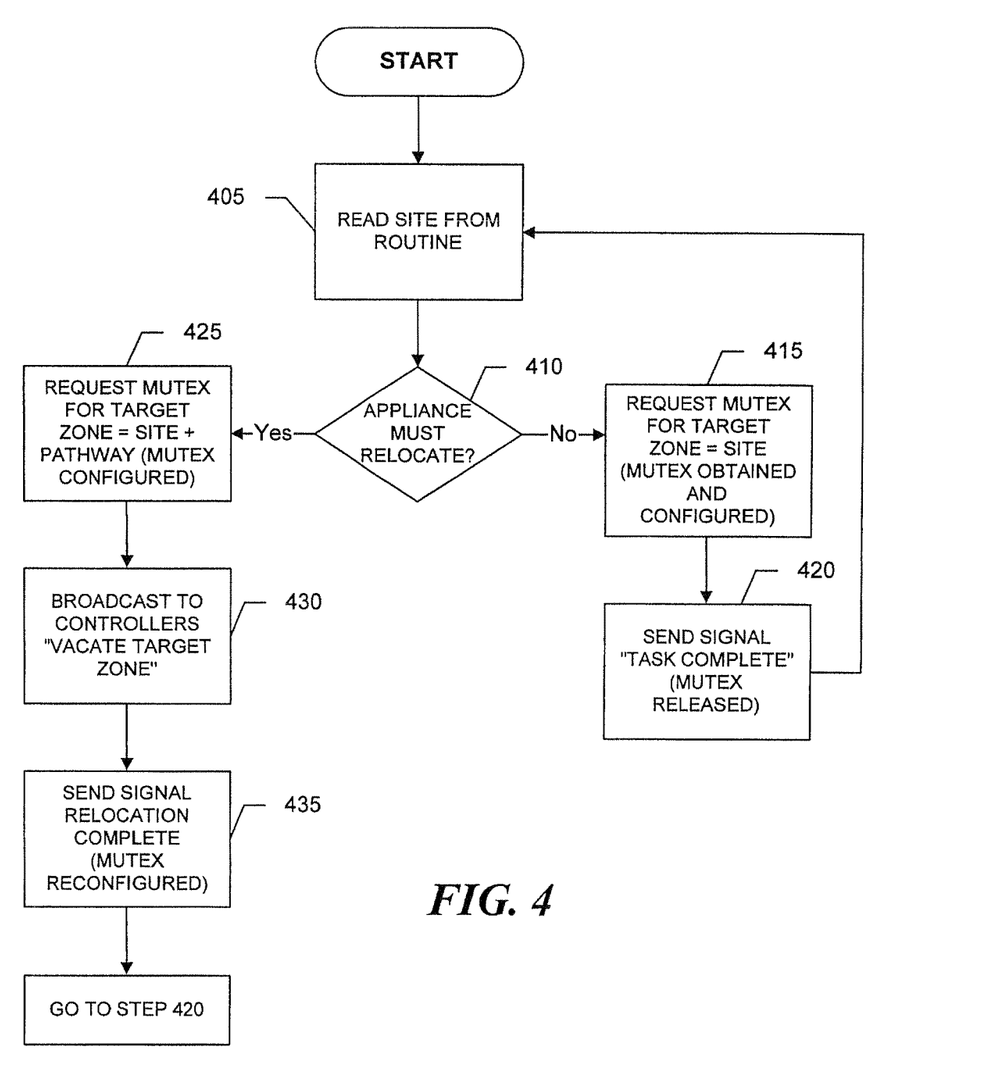
FIG. 4 is a flowchart demonstrating the steps followed by an appliance controller with respect to securing permission to enter or operate in a target zone.

FIG. 4 demonstrates the steps followed by each appliance controller in a workstation, such as is described in FIGS. 1-3, with respect to securing permission to enter or operate in a portion of the workspace. First, the controller receives direction from the respective routine (step 405). The routine provides to the controller a task having an associated site. Before beginning the task, the controller must first determine the desired target zone for its mutex. Accordingly, the controller decides whether it must relocate to begin the operation (step 410).

If the controller is already on the task site, the controller communicates with the mutex-control system to request a mutex configured to protect the site (step 415). The steps followed by the mutex-control function in accommodating the request are outlined in FIG. 5. The states of the mutexes are illustrated in FIG. 4 in parentheses. Once the mutex configured for the target zone has been obtained for the controller, the controller operates the appliance to complete its task. When the task is done, the controller sends a "task complete" signal to the mutex-control function (step 420). In response, the function releases the appliance's mutex protecting the site. Then, the controller returns to step 405 to begin the next task.

If the controller determines, in step 405, that the appliance must relocate before beginning the operation, the controller communicates with the mutex-control system to request a mutex configured to protect a target zone including the site prescribed by the routine plus a pathway from the appliance's present location to the site (step 425). Once the mutex configured for the target zone has been obtained for the controller, the controller broadcasts to the other controllers a command to vacate the target zone (step 430), to clear the target zone of any appliance idling in the way. Thereafter, once the controller has moved the appliance to the site, the controller sends a "relocation complete" signal to the mutex-control function (step 435) so the mutex can be reconfigured to protect only the task site, thus freeing the pathway locations for use by another appliance. When the task is completed, the controller advances to step 420 and notifies the mutex control function, which then releases the appliance's mutex.

Figure 5:
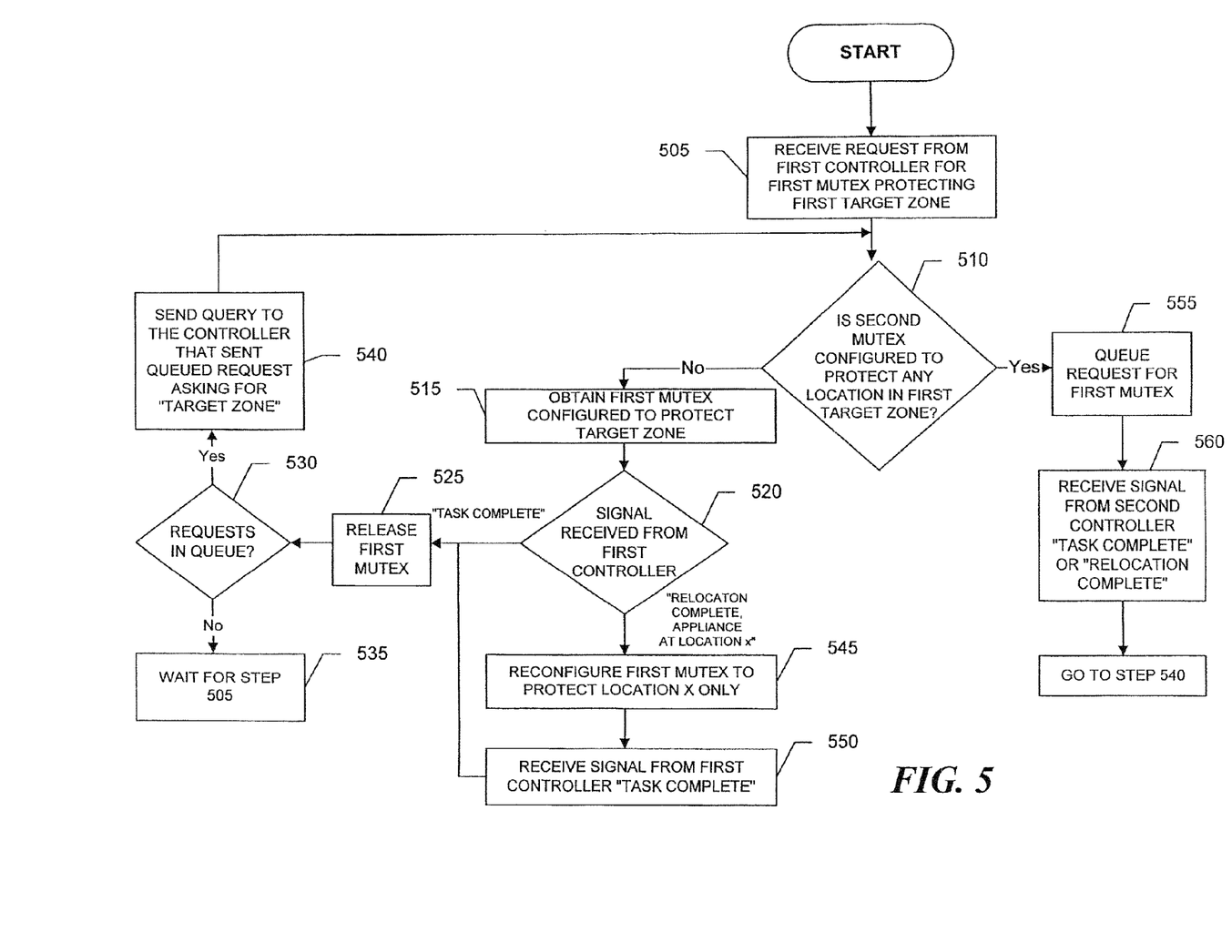
FIG. 5 is a flowchart demonstrating the steps followed by a mutex-control system in obtaining and configuring a mutex for an appliance controller.

FIG. 5 demonstrates the steps followed by the mutex-control function in a first configuration process, whereby a first mutex for a first appliance is configured and obtained for an appliance. For this discussion, the first appliance operates in a workstation having two appliances, such as is described in FIGS. 1-3. As used herein, the term first or second denotes a mutex, target zone, appliance controller, task or routine, as the case may be, associated with the first or second appliance.

The mutex-control system receives a request from the first controller for a first mutex protecting a first target zone (step 505). The mutex-control system checks whether a second mutex, configured and obtained for the second appliance, protects any location in the first target zone (step 510).

If not, the mutex-control function obtains for the first appliance a first mutex that is configured to protect the first target zone (step 515). When a signal is received from the first controller (step 520) indicating that the first appliance's task is complete, the mutex-control function releases the first mutex (step 525). The mutex-control function next determines whether there are any mutex requests in the queue (step 530). If not, the function waits (step 535) for another mutex request to restart at step 505. If there is a request in the queue, the mutex-control function queries the second controller to ascertain the second target zone (step 540) and then returns to step 510. The mutex-control function begins the next configuration process, for the second controller, analogously, with the roles of the first and second controllers and mutexes reversed.

Returning to the decision at step 520 of the first configuration process, if the signal received from the first controller in step 520 is "relocation complete, first appliance at location X," the mutex control function reconfigures the first mutex to protect the task site at location X (step 545). When the mutex control function later receives a "task complete" signal from the first controller (step 550), the process advances to step 525.

Returning to the decision at step 510 of the first configuration process, if the mutex-control function finds that a second mutex is held for some location in the first target range, the mutex control function queues the request for the first mutex (step 555). When the mutex-control function receives either a "task complete" or "relocation complete" signal from the second appliance (step 560), the function queries the first controller to ascertain the first target zone (step 540). The next iteration of the first configuration process then begins at step 510. The query is made because the first appliance may have moved to vacate a protected target zone, and thus, now require a larger target zone for its requested mutex. Alternatively, the mutex control function may keep track of the locations of the appliances and configure target zones based on requests for mutexes for target sites and on the locations of the corresponding appliances.

Mutex-protection of physical workspace works as well for automated workstations having more than two appliances. In such embodiments, the mutex control function allots a configurable mutex for each of the multiple appliances. Accordingly, at step 510 the mutex-control function checks whether mutexes protecting any location in the first target zone are held for any of the other appliances. After step 540, if a mutex cannot be obtained that is responsive to the request at the top of the queue, the function checks the requests queued for the other appliances. At step 560, a signal from any of the controllers other than the first controller triggers verification of the first target range in the following step 540. The target zone is verified in case one of the several appliances moves the first appliance through a vacate command (step 430), changing its location and thus the first target zone, while the first request is queued.

The appliances in general have successive access to any given site as each in turn has its mutex obtained, configured to protect the site. Mutex control of the workspace allows the appliances to complete their tasks concurrently so long as they don't need to invade protected space.

In another embodiment, one or more of the tools managed by the mutex-control function are not constrained by arm movement along a track and mutexes encompass corresponding target zones. Alternatively, or in addition, a single arm may move several tools, and each tool is allotted a configurable mutex. In yet another embodiment, the tools are moveable over a three-dimensional workspace, and the protected target zones have up to three dimensions. In any embodiment a target zone may extend slightly beyond a target site, by a predetermined distance or area to provide a buffer space for the appliances. For purposes of the invention, the term "mutex" is used in the context of the mutual exclusion control function described herein, and is not limited to the constructs of a particular computer operating system.

The processors or functions described herein can be implemented in software, firmware and/or hardware. The respective processors or functions may be performed by individual processors or groups of processors. Further, the processors or functions described or depicted separately may be combined in one or more processors or functions.

It will therefore be seen that the foregoing represents a highly advantageous approach to managing moveable appliances over a common physical space, especially with regard to preventing collisions between the appliances. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of managing multiple moveable appliances mobile over a common physical space by a computer system having at least one processor, comprising:
   a. defining, for a moveable appliance, a target spatial zone;
   b. determining, by a mutex-control system of the computer system, whether any location in the target spatial zone is protected by a mutex held by another appliance;
   c. obtaining for the moveable appliance a configurable mutex protecting the target spatial zone if the target spatial zone is not protected by any mutex held by another appliance;
   d. allowing the moveable appliance to occupy the target spatial zone if the target spatial zone is not protected by any mutex held by another appliance; and
   e. reconfiguring the configurable mutex obtained for the moveable appliance to reduce the target spatial zone after the moveable appliance no longer requires access to a portion of the target spatial zone.

2. The method of claim 1 further comprising the step of releasing the mutex obtained for the moveable appliance after the moveable appliance has completed a task.

3. The method of claim 1 wherein the target zone comprises a pathway and an operation site, further comprising reconfiguring the mutex obtained for the moveable appliance to protect only the operation site after the moveable appliance has moved through the target spatial zone to the site.

4. A method of managing multiple moveable appliances mobile over a common physical space, comprising the steps of:
   a. providing a first routine prescribing a task, for a first appliance, including a first target zone;
   b. providing a second routine prescribing a task, for a second appliance, including a second target zone that is different than the first target zone;
   c. obtaining for the first appliance, by a mutex-control system of a computer system having at least one processor, a first mutex protecting the first target zone;
   d. after obtaining the first mutex for the first appliance and before moving the second appliance to the second target zone, checking whether any mutex protects the second target zone;
   e. if no mutex protects the second target zone, obtaining for the second appliance a second mutex protecting the second target zone; and
   f. moving the respective appliances to the target zones for which mutexes are held.

5. The method of claim 4 wherein the first target zone comprises a pathway and an operation site, the method further comprising the steps of:
   a. altering the first mutex to protect only the operation site after moving the first appliance along the pathway to the operation site;
   b. controlling the first appliance to complete an operation at the site; and
   c. releasing the first mutex.

6. The method of claim 5 further comprising the steps of:
   a. after the first mutex is altered, checking whether any mutex protects the second target zone; and
   b. after the first mutex is released, checking whether any mutex protects the second target zone.

7. The method of claim 4 further comprising the steps of:
   a. controlling the first appliance to complete an operation after obtaining the first mutex protecting the first target zone; and
   b. releasing the first mutex protecting the first target zone.

8. The method of claim 7 further comprising the step of, after the first mutex is released, checking whether any mutex protects the second target zone.

9. A computer-implemented system managing moveable tools mobile over a common physical space, comprising:
   a. a mutex control system configured to
      i. designate a first mutex configurable to protect a variable first target spatial zone for a first appliance;
      ii. designate a second mutex configurable to protect a variable second target spatial zone for a second appliance, the second target zone being different than the first target zone;
   b. a first controller, controlling the first appliance, configured to
      iii. confer with the mutex control system before controlling the first appliance to move into or operate in the first target spatial zone;
      iv. control the first appliance to move into or operate in the first target spatial zone if the first mutex is configured to protect the first target spatial zone; and
   c. a second controller, controlling the second appliance, configured to
      v. confer with the mutex control system before controlling the second appliance to move into or operate in the second target spatial zone;
      vi. control the second appliance to move into or operate in the second target spatial zone if the second mutex is configured to protect the second target spatial zone.

10. The computer-implemented system of claim 9 wherein the mutex control system is configured to reconfigure the first mutex to protect a first site upon signal from the first controller.

11. The computer-implemented system of claim 10 wherein the first target spatial zone comprises a first pathway and a first site, the first controller being configured to
    a. make the first appliance traverse the first pathway to the first site while the first mutex is configured to protect the first target zone, and
    b. signal the mutex control system when the first appliance is at the first site, the mutex control system reconfiguring the first mutex to protect only the first site after the first appliance has reached the first site.

12. The computer-implemented system of claim 9 wherein the mutex control system is configured to release the first mutex upon signal from the first controller.

13. The computer-implemented system of claim 9 further comprising a scheduling system providing a first routine for the first appliance and a second routine for the second appliance.

14. The computer-implemented system of claim 13 further comprising a user interface whereby a user specifies at least one procedure, the scheduling system generating the first and second routines from the at least one procedure.

15. The computer-implemented system of claim 13 further comprising a user-interface configured to receive parameters from a user specifying at least one procedure, the scheduling system generating the first and second routines from the parameters.

16. The computer-implemented system of claim 9 further comprising a third controller configured to i. confer with the mutex control system before controlling a third appliance to move into or operate in the first or second target spatial zone, and ii. control the third appliance to move into or operate in the first or second target spatial zone if a third mutex is configured to protect a third target spatial zone, the mutex control system designating the third mutex, configurable to protect a variable third target spatial zone for the third appliance.

17. The computer-implemented system of claim 15 wherein first and second controllers are configured to operate the first and second appliances to perform biochemical procedures.

18. A laboratory workstation system managing tools moveable over a common physical space, comprising:
   a. a plurality of laboratory appliances moveable over a workspace that includes the common physical space;
   b. a mutex control system designating respective mutexes for the laboratory appliances to protect variable respective target spatial zones in the workspace; and
   c. respective controllers, controlling the laboratory appliances, configured to
      i. confer with the mutex control system before controlling the appliances to move into or operate in the respective target spatial zones, and
      ii. control the appliances to move into or operate in the respective target spatial zones that are protected by the respective mutexes.

19. The laboratory workstation system of claim 8 wherein
   a. the mutex control system is configured to reconfigure the mutex obtained for a given laboratory appliance to reduce the target spatial zone protected by the mutex after the laboratory appliance has moved through a portion of the target spatial zone; and
   b. the respective controllers are configured to confer with the mutex control system, after the mutex obtained for one of the plurality of laboratory appliances has been reconfigured, to check whether the reconfigured mutex frees space that is part of the target spatial zone with associated another of laboratory appliance.

20. The computer-implemented system of claim 10 wherein the mutex control system is further configured to:
   a. reconfigure the first mutex to reduce the first target spatial zone after the first appliance no longer requires access to a portion of the first target spatial zone; and
   b. after the first mutex is reconfigured, checking whether the first mutex protects the second target zone.

\* \* \* \* \*

UNITED STATES PATENT AND TRADEMARK OFFICE
CERTIFICATE OF CORRECTION

PATENT NO. : 8,473,085 B2
APPLICATION NO. : 12/112466
DATED : June 25, 2013
INVENTOR(S) : James Sim et al.

Page 1 of 1

It is certified that error appears in the above-identified patent and that said Letters Patent is hereby corrected as shown below:

In the Claims:

Col. 10, line 4 should read: "19. The laboratory workstation system of claim 8̶18 wherein"

Signed and Sealed this
Third Day of September, 2013

Teresa Stanek Rea
*Acting Director of the United States Patent and Trademark Office*